United States Patent
Caille et al.

(10) Patent No.: US 8,501,954 B2
(45) Date of Patent: Aug. 6, 2013

(54) ASYMMETRIC PROCESS FOR MAKING SUBSTITUTED 2-AMINO-THIAZOLONES

(75) Inventors: Seb Caille, Moorpark, CA (US); Sheng Cui, Camarillo, CA (US); Xiang Wang, Thousand Oaks, CA (US); Margaret Faul, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 55 days.

(21) Appl. No.: 13/056,583

(22) PCT Filed: Jul. 28, 2009

(86) PCT No.: PCT/US2009/051929
§ 371 (c)(1),
(2), (4) Date: Jan. 28, 2011

(87) PCT Pub. No.: WO2010/014586
PCT Pub. Date: Feb. 4, 2010

(65) Prior Publication Data
US 2011/0178307 A1    Jul. 21, 2011

Related U.S. Application Data

(60) Provisional application No. 61/084,549, filed on Jul. 29, 2008.

(51) Int. Cl.
*C07D 277/14* (2006.01)
(52) U.S. Cl.
USPC .......................................... 548/184

(58) Field of Classification Search
None
See application file for complete search history.

(56) References Cited

U.S. PATENT DOCUMENTS

2007/0117985 A1    5/2007    Bunel et al.

FOREIGN PATENT DOCUMENTS

| WO | WO-2005/116002 A | 12/2005 |
| WO | WO-2007/061661 A | 5/2007 |
| WO | WO 2009/002445 A1 | 12/2008 |

OTHER PUBLICATIONS

Harden et al. J. Med. Chem. (1978), vol. 21(1), pp. 82-87.*
Schreiner et al. J. Org. Chem. (2002), 67, 8299-8304.*
International Search Report mailed Sep. 21, 2009 in PCT/US2009/051929, 2 pages.
Chinese Office Action and Search Report mailed Oct. 23, 2012 in JP Application 200980128488.3.
Caille, et al., "New methods for the Synthesis of 2-Aminothiazolones", *The Journal of Organic Chemistry*, 2008, vol. 73, issue 5, pp. 2003-2006.

* cited by examiner

*Primary Examiner* — Nyeemah A Grazier
(74) *Attorney, Agent, or Firm* — Foley & Lardner LLP

(57) ABSTRACT

The invention provides two process for synthesizing substituted aminothiazolone compounds as inhibitors of 11-β-hydroxy steroid dehydrogenase type 1. The processes allow the stereoselective synthesis of the desired compounds without the use of stoichiometric amounts of chiral catalysts.

5 Claims, No Drawings

ASYMMETRIC PROCESS FOR MAKING SUBSTITUTED 2-AMINO-THIAZOLONES

BACKGROUND OF THE INVENTION

The present invention relates generally to novel organic synthetic methodology and its application for providing compounds that are useful as inhibitors of 11β-hydroxy steroid dehydrogenase type 1.

Hydroxysteroid dehydrogenases (HSDs) regulate the occupancy and activation of steroid hormone receptors via the interconvertsion between steroid hormones and its inactive form. For a recent review, see Nobel et al., Eur. J. Biochem. 2001, 268:4113-4125.

There exist numerous classes of HSDs. The 11-beta-hydroxysteroid dehydrogenases (11 β-HSDs) is an oxidoreductase whose oxidative component metabolises biologically active glucocorticosteroid (such as cortisol and corticosterone), to the inactive C-11 oxidised metabolites, cortisone and 11-dehydrocorticosternone. Ragosh, et al., J. Endocrinology, 1997, 155:171-180.

The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

The 11β-HSD1 isoform is also present in pancreatic islet cells where it is implicated to play a role in controlling insulin release. Oppermann et al., J. Biological Chemistry, 2000, 275(45): 34841-34844. Glucocorticoid hormones such as cortisol (active form) and cortisone (inactive keto form) play a critical role in the regulation of carbohydrate metabolism. Increased levels of cortisol, promotes gluconeogenesis and inhibits insulin release. This results in high serum glucose levels characteristic of diabetic pathogenesis. Conversely, the known 11β-HSD1 inhibitor carbenoxolone reverses the inhibition of insulin release by cortisol in a dose dependent manner and further enhances insulin sensitivity. These observations indicate that 11β-HSD1 in pancreatic islet cells plays an important role in regulating glucocorticoid metabolism and release of insulin. Thus, 11β-HSD1 is an important enzyme target for the development of anti-diabetic therapeutic agents.

The C5-substituted 2-amino thiazolinones have been shown to be potent inhibitors of 11β-HSD1. In particular, 5S-2-(bicycle[2.2.1]heptan-2-ylamino)-5-isopropyl-5-methylthiazol-4(5H)-one, which is shown below, is a potent nanomolar inhibitor of this enzyme. Current synthetic routes to prepare this 2-aminothiazolone analog entail multiple steps and the use of high equivalents of an expensive chiral catalyst for the enantioselective addition of the isopropyl group to the C-5 atom of the parent 2-aminothiazolone.

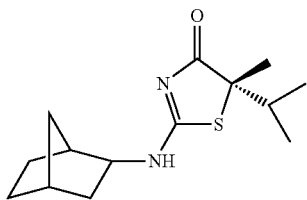 [SMILES: CC(C)[C@]1(C)SC(NC2CC3CCC2C3)=NC1=O]

There appears, therefore, a need for alternative synthetic methodology that would allow the facile and stereoselective preparation of 5S-2-(bicycle[2.2.1]heptan-2-ylamino)-5-isopropyl-5-methylthiazol-4(5H)-one and related compounds employing commercially available starting materials and small quantities of a chiral catalyst.

SUMMARY OF THE INVENTION

The present invention satisfies this need and others by providing efficient synthetic routes for the preparing a compound of formula 2, its tautomer, stereoisomer or pharmaceutically acceptable salts thereof.

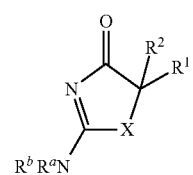

2

Thus, one embodiment of the invention is a method for making a compound of formula 2 by reacting a compound of formula 1:

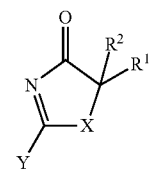

1 with a compound of formula $R^aR^bNH$.

In formulae 1 and 2, the variable X is selected from the group consisting of S, O, and NR, whilst Y is either R"C(O)NH, or SR". In one embodiment, X is a nitrogen atom and R is selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

In various embodiments of the present invention, R" in leaving group "Y" is selected from the group consisting of $(C_1-C_8)$alkyl, aryl, $(C_3-C_8)$cycloalkyl, and aryl$(C_1-C_6)$alkyl.

The C-5 substituents $R^1$ and $R^2$ are independently selected from the group consisting of hydrogen, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl, with the proviso that $R^1$ and $R^2$ are not simultaneously hydrogen atoms.

In various embodiments of the present invention, substituents $R^a$ and $R^b$ of compound $R^aR^bNH$ can either be the same or different groups. Thus, $R^a$ is selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Substituent $R^b$ is selected from the group consisting of $(C_1-C_8)$alkyl, $(C_2-C_8)$alkenyl, $(C_2-C_8)$alkynyl, $(C_1-C_4)$ alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

In another embodiment, the present invention provides a method for making the compound of formula 1 by reacting a compound of formula 3 with a compound of formula Y—CN. The variables X, $R^1$ and $R^2$ in formula 3 are as defined above:

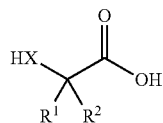

3

In another embodiment, the present invention provides a process for preparing a compound of formula 4 its tautomer, stereoisomer, or pharmaceutically acceptable salt thereof:

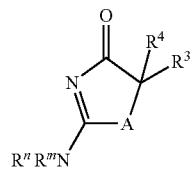

4

The process comprises reacting a compound of formula 5:

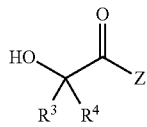

5 with a compound of formula 6:

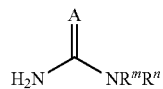

6

In formulae 4, 5 and 6, the variable A is selected from the group consisting of S, O, and $NR^5$, whilst Z is selected from the group consisting of halogen, $OR^6$ and $SR^6$.

In one embodiment, X is a nitrogen atom and $R^5$ is selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, substituted or unsubstituted heteroaryl, substituted or unsubstituted aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

In embodiments where leaving group Z is $OR^6$ and $SR^6$, $R^6$ is selected from the group consisting of $(C_1-C_8)$alkyl, pentafluorophenyl, nitrophenyl, di-nitrophenyl, $CF_3$-phenyl, p-toluenesulfonyl, and methanesulfonyl.

Furthermore, substituents $R^3$ and $R^4$ at C-5 are each independently selected from the group consisting of hydrogen, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl; with the proviso that $R^3$ and $R^4$ are not simultaneously hydrogen atoms.

In various embodiments of the present invention, substituents $R^m$ and $R^n$ of compound 6 can either be the same or different groups. Thus, $R^m$ is selected from the group consisting of hydrogen, hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

Similarly $R^n$ is selected from the group consisting of $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

DETAILED DESCRIPTION

Definitions

As used herein, the terms have the following meanings:

The term "alkyl" as used herein refers to a straight or branched chain, saturated hydrocarbon having the indicated number of carbon atoms. For example, $(C_1-C_6)$alkyl is meant to include, but is not limited to methyl, ethyl, propyl, isopropyl, butyl, sec-butyl, text-butyl, pentyl, isopentyl, neopentyl, hexyl, isohexyl, and neohexyl. An alkyl group can be unsubstituted or optionally substituted with one or more substituents as described herein throughout.

The term "alkenyl" as used herein refers to a straight or branched chain unsaturated hydrocarbon having the indicated number of carbon atoms and at least one double bond. Examples of a $(C_2-C_8)$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" as used herein refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" as used herein refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the $C_1$-$C_6$ alkyl group's hydrogen atoms is replaced with an amine of formula —N($R^c$)$_2$, wherein each occurrence of $R^c$ is independently —H or ($C_1$-$C_6$)alkyl. Examples of aminoalkyl groups include, but are not limited to, —CH$_2$NH$_2$, —CH$_2$CH$_2$NH$_2$—, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N (CH$_3$)$_2$, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocyclopheptene, dodecahydroheptalene, decahydroheptalene, octahydroheptalene, hexahydroheptalene, and tetrahydroheptalene, (1s,3s)-bicyclo[1.1.0]butane, bicycle[1.1.1]pentane, bicycle[2.1.1]hexane, Bicycle[2.2.1] heptane, bicycle[2.2.2]octane, bicycle[3.1.1]heptane, bicycle[3.2.1]octane, bicycle[3.3.1]nonane, bicycle[3.3.2]decane, bicycle[3.3.]undecane, bicycle[4.2.2]decane, bicycle[4.3.1] decane. A cycloalkyl group can be unsubstituted or optionally substituted with one or more substituents as described herein below.

The term "halo" as used herein refers to —F, —Cl, —Br or —I.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —CH$_2$—CH$_2$—O—CH$_3$, —CH$_2$—CH$_2$—NH—CH$_3$, —CH$_2$—CH$_2$—N (CH$_3$)—CH$_3$, —CH$_2$—S—CH$_2$—CH$_3$, —CH$_2$—CH$_2$—S (O)—CH$_3$, —CH$_2$—CH$_2$—S(O)$_2$—CH$_3$, and —CH$_2$—CH=N—OCH$_3$. Up to two heteroatoms can be consecutive, such as, for example, —CH$_2$—NH—OCH$_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —CH$_2$OH (one carbon atom and one heteroatom replacing a carbon atom) and —CH$_2$SH.

To further illustrate the definition of a heteroalkyl group, where the heteroatom is oxygen, a heteroalkyl group can be an oxyalkyl group. For instance, ($C_2$-$C_5$)oxyalkyl is meant to include, for example —CH$_2$—O—CH$_3$ (a $C_3$-oxyalkyl group with two carbon atoms and one oxygen replacing a carbon atom), —CH$_2$CH$_2$CH$_2$CH$_2$OH, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH₂CH₂CH₂CH₂OH, —CH₂CH₂CH₂CH₂OH, —CH₂CH₂CH₂CH₂CH₂OH, and branched versions thereof.

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including: —OR$^{a\prime}$, =O, =NR$^{a\prime}$, =N—OR$^{a\prime}$, —NR$^{a\prime}$R$^{a\prime\prime\prime}$, —SR$^{a\prime}$, -halo, —SiR$^{a\prime}$R$^{a\prime\prime}$R$^{a\prime\prime\prime}$, —OC(O)R$^{a\prime}$, —C(O)R$^{a\prime}$, —CO₂R$^{a\prime}$, —CONR$^{a\prime}$R$^{a\prime\prime\prime}$, —OC(O)NR$^{a\prime}$R$^{a\prime\prime\prime}$, —NR$^{a\prime\prime\prime}$C(O)R$^{a\prime}$, —NR$^{a\prime\prime\prime\prime}$C(O)NR$^{a\prime}$R$^{a\prime\prime\prime}$, —NR$^{a\prime\prime\prime\prime}$SO₂NR$^{a\prime}$R$^{a\prime\prime\prime}$, —NR$^{a\prime}$CO₂R$^{a\prime}$, —NHC(NH₂)=NH, —NR$^{a\prime}$C(NH₂)=NH, —NHC(NH₂)=NR$^{a\prime}$, —S(O)R$^{a\prime}$, —SO₂R$^{a\prime}$, —SO₂NR$^{a\prime}$ R$^{a\prime\prime\prime}$, —NR$^{a\prime}$SO₂R$^{a\prime}$, —CN and —NO₂, in a number ranging from zero to three, with those groups having zero, one or two substituents being exemplary. R$^{a\prime}$, R$^{a\prime\prime}$ and R$^{a\prime\prime\prime}$ each independently refer to hydrogen, unsubstituted (C₁-C₈)alkyl, unsubstituted hetero(C₁-C₈)alkyl, unsubstituted aryl and aryl substituted with one to three substituents selected from -halo, unsubstituted alkyl, unsubstituted alkoxy, unsubstituted thioalkoxy and unsubstituted aryl(C₁-C₄)alkyl. When R$^{a\prime}$ and R$^{a\prime\prime}$ are attached to the same nitrogen atom, they can be combined with the nitrogen atom to form a 5-, 6- or 7-membered ring. For example, —NR$^{a\prime}$R$^{a\prime\prime\prime}$ can represent 1-pyrrolidinyl or 4-morpholinyl. Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted. From the above discussion of substituents, one of skill in the art will understand that the term "alkyl" is meant to include groups such as trihaloalkyl (e.g., —CF₃ and —CH₂CF₃).

Exemplary substituents for the alkyl and heteroalkyl radicals include but are not limited to —OR$^{a\prime}$, =O, =NR$^{a\prime}$, =N—OR$^{a\prime}$, —NR$^{a\prime}$R$^{a\prime\prime\prime}$, —SR$^{a\prime}$, -halo, —SiR$^{a\prime}$R$^{a\prime\prime}$R$^{a\prime\prime\prime}$, —OC(O)R$^{a\prime}$, —C(O)R$^{a\prime}$, —CO₂R$^{a\prime}$, —CONR$^{a\prime}$R$^{a\prime\prime\prime}$, —OC(O)NR$^{a\prime}$R$^{a\prime\prime\prime}$, —NR$^{a\prime\prime\prime}$C(O)R$^{a\prime}$, —NR$^{a\prime\prime\prime\prime}$C(O)NR$^{a\prime}$R$^{a\prime\prime\prime}$, —NR$^{a\prime\prime\prime\prime}$SO₂NR$^{a\prime}$R$^{a\prime\prime\prime}$, —NR$^{a\prime\prime\prime}$CO₂R$^{a\prime}$, —NHC(NH₂)=NH, —NR$^{a\prime}$ C(NH₂)=NH, —NHC(NH₂)=NR$^{a\prime}$, —S(O)R$^{a\prime}$, —SO₂R$^{a\prime}$, —SO₂NR$^{a\prime}$R$^{a\prime\prime\prime}$, —NR$^{a\prime\prime\prime}$SO₂R$^{a\prime}$, —CN and —NO₂, where R$^{a\prime}$, R$^{a\prime\prime}$ and R$^{a\prime\prime\prime}$ are as defined above. Typical substituents can be selected from: —OR$^{a\prime}$, =O, —NR$^{a\prime}$R$^{a\prime\prime\prime}$, -halo, —OC(O)R$^{a\prime}$, —CO₂R$^{a\prime}$, —C(O)NR$^{a\prime}$R$^{a\prime\prime\prime}$, —OC(O)NR$^{a\prime}$R$^{a\prime\prime\prime}$, —NR$^{a\prime\prime\prime}$C(O)R$^{a\prime}$, —NR$^{a\prime\prime\prime}$CO₂R$^{a\prime}$, —NR$^{a\prime\prime\prime\prime}$SO₂NR$^{a\prime}$R$^{a\prime\prime\prime}$, —SO₂R$^{a\prime}$, —SO₂NR$^{a\prime}$R$^{a\prime\prime\prime}$, —NR$^{a\prime\prime\prime}$SO₂R$^{a\prime}$—CN and —NO₂.

Similarly, substituents for the aryl and heteroaryl groups are varied and selected from: -halo, —OR$^{e\prime}$, —OC(O)R$^{e\prime}$, —NR$^{e\prime}$R$^{e\prime\prime\prime}$, —SR$^{e\prime}$, —R$^{e\prime}$, —CN, —NO₂, —CO₂R$^{e\prime}$ C(O)NR$^{e\prime}$R$^{e\prime\prime\prime}$, —C(O)R$^{e\prime}$, —OC(O)NR$^{e\prime}$ R$^{e\prime\prime\prime}$, —NR$^{e\prime\prime\prime}$C(O)R$^{e\prime}$, —NR$^{e\prime\prime\prime}$CO₂R$^{e\prime}$, —NR$^{e\prime\prime\prime\prime}$C(O)NR$^{e\prime}$R$^{e\prime\prime\prime}$, —NR$^{e\prime\prime\prime\prime}$SO₂NR$^{e\prime}$R$^{e\prime\prime\prime}$, —NHC(NH₂)=NH, —NR$^{e\prime}$C(NH₂)=NH, —NH—C(NH₂)=NR$^{e\prime}$, —S(O)R$^{e\prime}$, —SO₂R$^{e\prime}$, SO₂NR$^{e\prime}$ R$^{e\prime\prime\prime}$, —NR$^{e\prime\prime\prime}$SO₂R$^{e\prime}$, —N₃, —CH(Ph)₂, perfluoroalkoxy and perfluoro(C₁-C₄)alkyl, in a number ranging from zero to the total number of open valences on the aromatic ring system; and where R$^{e\prime}$, R$^{e\prime\prime\prime}$ and R$^{e\prime\prime\prime\prime}$ are independently selected from hydrogen, unsubstituted (C₁-C₈)alkyl, unsubstituted hetero(C₁-C₈)alkyl, unsubstituted aryl, unsubstituted heteroaryl, unsubstituted aryl(C₁-C₄)alkyl and unsubstituted aryloxy(C₁-C₄)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein throughout may optionally be replaced with a substituent of the formula -T-C(O)—(CH₂)$_q$—U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -J-(CH₂)$_r$—K—, wherein J and K are independently —CH₂—, —O—, —NH—, —S—, —S(O)—, —S(O)₂—, —S(O)₂NR$^{f\prime}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X—(CH₂)$_t$—, where s and t are independently integers of from 0 to 3, and X is —O—, —NR$^{f\prime}$, —S—, —S(O)—, —S(O)₂—, or —S(O)₂NR$^{a\prime}$—. The substituent R$^{f\prime}$ in —NR$^{f\prime}$ and —S(O)₂NR$^{f\prime}$— is selected from hydrogen or unsubstituted (C₁-C₆)alkyl.

It is to be understood that if a —CO₂H substituent is present, the —COON group can optionally be replaced with bioisosteres such as:

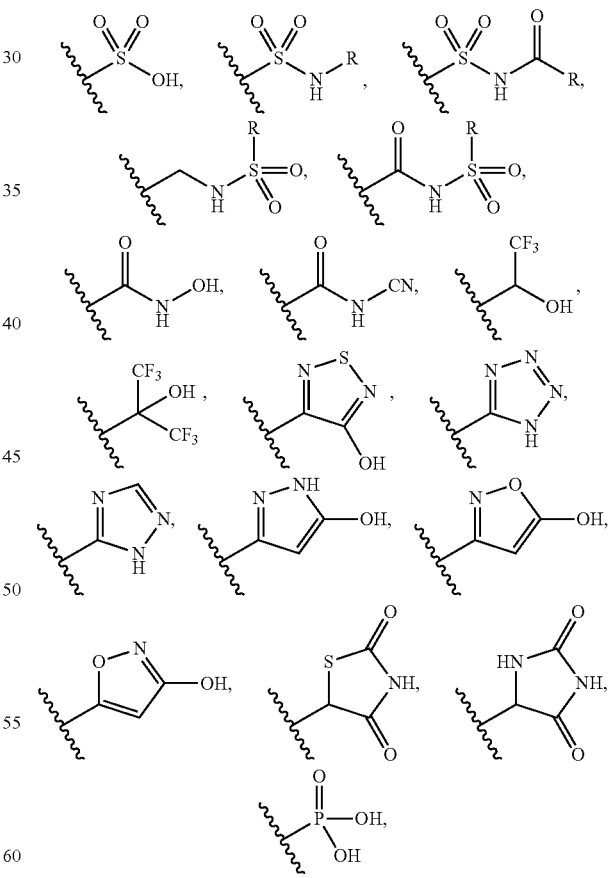

and the like. See, e.g., *The Practice of Medicinal Chemistry*; Wermuth, C. G., Ed.; Academic Press: New York, 1996; p. 203.

It is also understood that coupling of two reagents frequently requires a functional group on one of the reagent to be activated prior to coupling. In this regard, the term "activation" denotes the standard use of conventional activating reagents. For example, a carboxyl group is activated via carboxyl activating agents. Reagents comprising a carboxyl group substituent may be activated by a variety of standard activating agents, such as thionyl chloride, phosphory chloride, diimidazolcarbonyl, N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP), bis(2-oxo-3-oxazolidinyl)phosphine chloride (BOPCl), DEPBT (3-(Diethoxy-phosphoryloxy)-3H-benzo[d][123]triazin-4-one), BEP (2-bromo-1-ethyl pyridinium tetrafluoroborate), HATU (N,N,N',N'-tetramethyl-O-(7-azabenzotriazol-1-yl)uronium hexafluorophosphate), TBTU (N,N,N',N'-tetramethyl-O-(benzotriazol-1-yl)uronium tetrafluoroborate), PyBop (benzotriazol-1-yloxy)tripyrrolidinophosphonium hexafluorophosphate), and the like.

The compound of formula 2 can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound of formula 2, including tautomeric forms of the compound.

Compounds of formula 2 have asymmetric centers and therefore exist in different enantiomeric and diastereomeric forms. A compound can exist in the form of an optical isomer or a diastereomer. Accordingly, the invention encompasses compounds of formula 2 in the forms of their optical isomers, diastereomers and mixtures thereof, including racemic mixtures.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

Process of Preparation

The present invention provides two processes for the facile synthesis of 5-substituted 2-aminothiazolones as shown below in Schemes 1 and 2.

As would be readily recognized by a skilled artisan, the processes described herein allow the synthesis of various heterocycles represented by formula 2. Thus, in one embodiment, X is a sulfur or oxygen atom. In yet another embodiment, X is a substituted or unsubstituted amine, such as an alkyl amine or a substituted or unsubstituted aryl amine.

The identity of substituent groups $R^1$ and $R^2$ at position C-5 of the 2-amino thiazolone analog depends on the choice of the starting ketone (1). In one embodiment, $R^1$ and $R^2$ are both independently ($C_1$-$C_3$)alkyl groups. Examples of such groups include methyl, ethyl, propyl, and isopropyl groups. In one embodiment, the C-5 carbon atom bears a methyl and an isopropyl group. Alternatively, the present invention also contemplates the preparation of a compound of formula 2 where $R^1$ and $R^2$ are the same group or a compound where $R^1$ is alkyl and $R^2$ is an optionally substituted aryl, heteroaryl, alkynyl, alkenyl, cycloalkyl, or a heterocycloalkyl group.

The compound of formula 2 is obtained by displacing Y from the compound of formula 1 using an unsubstituted or substituted amine($NR^aR^b$). In one embodiment, therefore, $R^a$ is a hydrogen while $R^b$ is a cycloalkyl or a bicycloalkyl as described hereinabove. Thus, in some embodiments, $R^b$ is an unsubstituted bicycloalkane such as, for example, a norbornyl group (bicyclo[2.2.1]heptane).

In a further embodiment, leaving group Y in formula 1 is an alkyl or aryl amide. Alternatively, the leaving group is an alkyl or aryl thiol.

In still another embodiment, the inventive process provides a compound of formula 4 obtained via an intramolecular displacement reaction. Thus, A in formula 4 is either a sulfur atom, an oxygen atom or a substituted or unsubstituted amine obtained by reacting an appropriate guanidine moiety with the acyl halide of formula 5.

As mentioned above, the identity of substituent groups $R^3$ and $R^4$ at position C-5 of the 2-amino thiazolone analog depends on the choice of the starting ketone. In one embodiment, for instance, $R^3$ is methyl and $R^4$ is an isopropyl group.

In another embodiment, the leaving group Z in formula 5 is a halogen, an oxygen ester, a mesolate, a tosylate or a thioester. Other suitable leaving groups are well known in the art and are contemplated herein. When Z is a halogen, Z can be chlorine, bromine or an iodine.

The 5-substituted-2-aminothiazolones prepared using the inventive methodologies involve the asymmetric hydrocyanation reaction of an appropriate ketone to give a cyanohydrin. According to one aspect of the invention a metal catalyst and an appropriate chiral ligand is used for preparing the chiral cyanohydrin. While several catalyst-ligand pairs are well known in the art, in one embodiment the transition metal is aluminum having a formal oxidation state of +3.

Ligands suitable for use with the metal catalyst include monodentate and multidentate ligands. In one embodiment, when the ligand is monodentate, more than one monodentate ligand is typically utilized for coordinating to the metal.

In accordance with the normal definition in the art, "multidentate" refers to a ligand that coordinates to the transition metal or its ion through two or more atoms. Thus, for example, the ligand can be bidentate or tridentate. In another embodiment, the ligand is bidentate. An exemplary bidentate ligand is a phosphine that coordinates to the metal or ion through two phosphorus atoms. Other examples of bidentate ligands comprise, for example, various pairings of phosphorus, sulfur, nitrogen, and oxygen donor atoms. In still another embodiment the bidentate ligand is an analog of bromophenol blue.

The amount of catalyst can range in one embodiment from about 0.001 mol % to about 10 mol %. In another embodiment, the amount can range from about 0.01 mol % to about 5 mol %. In still another embodiment, the amount can range from about 0.1 mol % to about 1.0 mol %. An exemplary amount of catalyst is about 0.5 mol %.

Compounds of formulae 2 and 4, in addition to exhibiting chirality at C5, may contain one or more other stereochemical centers, and thereby provide for the presence of diastereomers. The invention contemplates the preparation of all such stereochemical isomers of a compound of formulae 2 and 4.

If needed, further purification and separation of enantiomers and diastereomers can be achieved by routine procedures known in the art. Thus, for example, the separation of enantiomers of a compound of formula 2 and 4 can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

As generally described above, the process is performed in the presence of a base. The base can be any convenient organic or inorganic compound. Typically, the base is not nucleophilic. Thus, in one embodiment, the base is selected from carbonates, phosphates, alkoxides, and salts of disilazanes.

The process of the invention, when performed as described herein, can be substantially complete after several minutes to after several hours depending upon the nature and quantity of reactants and reaction temperature, for example. The determination of when the reaction is substantially complete can be conveniently evaluated by ordinary techniques known in the art such as, for example, HPLC, LCMS, TLC, and $^1$H NMR.

EXAMPLES

The present invention is not to be limited in scope by the specific embodiments disclosed in the examples, which are intended to be illustrations of a few embodiments of the invention, nor is the invention to be limited by any embodiments that are functionally equivalent within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

Intermolecular displacement approach to the synthesis of 5-disubstituted-2-aminothiazolones In one embodiment of the present invention, synthesis of the target compound generally involves the asymmetric hydrocyanation of 3-methyl butane-2-one (1), to give the corresponding R-2-hydroxy-3-methyl butanenitrile. Activation of the hydroxyl by forming a mesolate prior to nucleophilic displacement with sodium sulfide results in the formation of the corresponding 2-mercapto-2,3-dimethylbutane nitrile having opposite (S) stereochemistry at C-2. Hydrolysis of the cyano group followed by reaction of the resultant carboxylic acid (5) with methylisothiocyanate and cyclization of the resultant adduct gives (S)-5-methyl-2-(methylthio)thiazole-4(5H)-one (6). The target compound is obtained by reacting (6) with S-aminonorbornane. This reaction sequence is illustrated in Scheme 1 below, and the following examples refer to the numbering scheme employed in the reaction sequence.

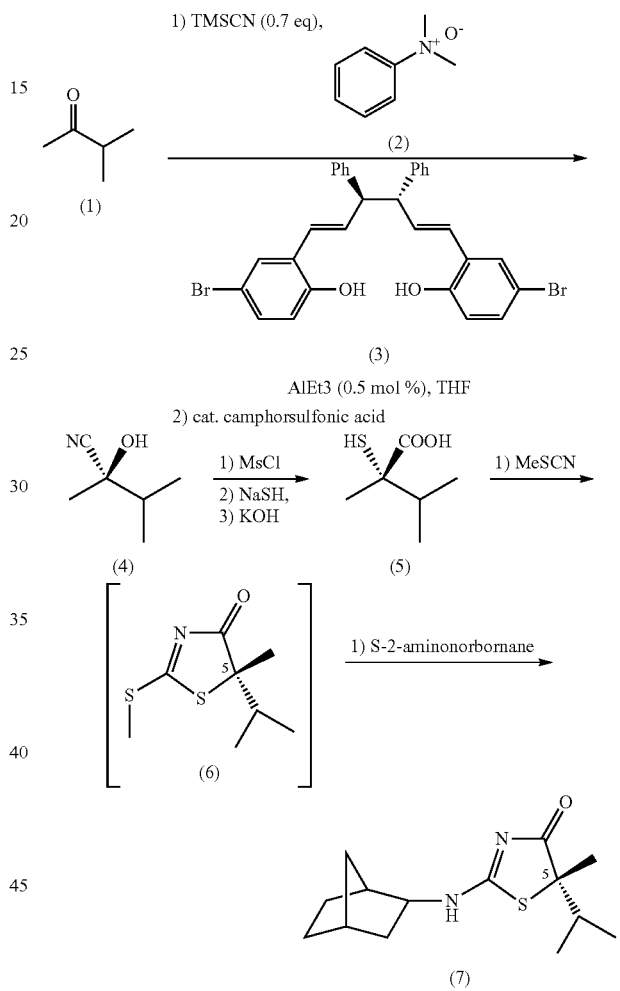

Example 1

Preparation of (R)-2,3-Dimethyl-2-(trimethylsilyloxy)butanenitrile (4)

TMSCN (28.8 g, 0.29 mol) and N,N-dimethylaniline oxide (0.2 g, 0.0015 mol) were dissolved in THF (75 mL) and the resultant solution was stirred for 1 h at 23° C. under an atmosphere of nitrogen. 3-Methylbutan-2-one (50.0 g, 0.58 mol) was added via syringe and the mixture was cooled to −30° C. 2-(E)-((1S,2S)-2-((E)-5-bromo-2-hydroxybenzylideneamino)-1,2-diphenylethylimino)methyl)-4-bromophenol (1.67 g, 0.0029 mol) and triethylaluminum (0.33 g, 0.0029 mol) were added and the reaction mixture was stirred for 24 h. The mixture was warmed to 23° C. and concentrated (30 mmHg). The residue was distilled under reduced pressure (30 mmHg, 80° C.) to yield 47.2 g (88%) of the title compound. $^1$H NMR (400 MHz, CDCl$_3$) δ 1.86 (septaplet, 1H, J=4 Hz), 1.53 (s, 3H), 1.04 (d, 3H, J=4 Hz), 1.02 (d, 3H, J=4 Hz), 0.25 (s, 9H); $^{13}$C NMR (100 MHz, CDCl$_3$) δ 121.5, 73.4, 39.1, 26.0, 17.1, 16.9, 1.15; IR (neat): 2969, 1375, 1254, 1160, 991, 841, 755 cm$^{-1}$; Exact Mass (C$_9$H$_{19}$NOSi+Na): calculated=208.1128, measured=208.1130. [α]$_D$ at 23° C. and 21.0 g/L in CDCl$_3$=+12.19. Chiral GC: 85.8% ee.

Example 2

Preparation of (R)-2-Cyano-3-methylbutan-2-ylmethanesulfonate (R)-2,3-Dimethyl-2-(trimethylsilyloxy)butanenitrile (11.0 g, 0.059 mol) was dissolved in 2-MeTHF (110 mL) under an atmosphere of nitrogen. Water (2.2 mL) and CSA (0.68 g, 0.00295 mol) were added and the solution was stirred for 3 h. The reaction mixture was treated with saturated aqueous NaHCO$_3$ (100 mL), the phases were separated and the aqueous phase was extracted with 2-MeTHF (2×50 mL). The combined organic phases were washed with brine, dried (Na$_2$SO$_4$) and concentrated under reduced pressure (~1 mmHg).

The residue was dissolved in 2-MeTHF (100 mL) under an atmosphere of nitrogen. Et$_3$N (10.9 mL, 0.077 mol) and MsCl (5.98 mL, 0.077 mol) were added via syringes and the reaction mixture was stirred for 2 h. The mixture was treated with saturated aqueous NaHCO$_3$ (100 mL), the phases were separated and the aqueous phase was extracted with 2-MeTHF (3×50 mL). The combined organic phases were washed with brine, dried (Na$_2$SO$_4$) and concentrated under reduced pressure. Chromatographic purification (70 g silica gel, 10-20% EtOAc/Hexanes) of the residual material yielded 10.36 g (92%) of the title compound. $^1$H NMR (400 MHz, CDCl$_3$) δ 3.17 (s, 3H), 2.24 (septuplet, 1H, J=8 Hz), 1.89 (s, 3H), 1.14 (t, 6H, J=8 Hz); $^{13}$C NMR (100 MHz, CDCl$_3$) δ 116.7, 82.6, 39.7, 37.8, 23.1, 16.7, 16.6; IR (neat): 2979, 1466, 1358, 1180, 1048, 901, 805 cm$^{-1}$; Exact Mass (C$_7$H$_{13}$NO$_3$S+Na): calculated=214.0508, measured=214.0510. [α]$_D$ at 23° C. and 12.5 g/L in CDCl$_3$=+14.98. Chiral GC: 85.44% ee.

Example 3

Preparation of (S)-2-mercapto-2,3-dimethylbutanoic acid (5)

NaSH hydrate (1.2 g, 0.097 mol) was dissolved in water (62 mL) and the solution was warmed to 45° C. under an atmosphere of nitrogen. The pH of the aqueous solution was adjusted to 8-9 by addition of 0.31 mL of concentrated aqueous HCl. (R)-2-Cyano-3-methylbutan-2-ylmethanesulfonate (3.1 g, 0.016 mol) was added via syringe and the reaction mixture was stirred for 20 h. To the resultant solution was added KOH (62 g, 1.1 mol) as a solid and the mixture was warmed to 95° C. The solution was stirred for 18 h and cooled to 23° C. The mixture was poured on a chilled (0° C.) aqueous concentrated HCl (60 mL) solution (the internal temperature of the resultant aqueous mixture was kept under 50° C.). The solution was extracted using IPAC (3×50 mL). The combined organic phases were washed with brine, dried (Na$_2$SO$_4$) and concentrated under reduced pressure. Chromatographic purification (15 g silica gel, 10-50% EtOAc/Hexanes) of the residual material yielded (S)-2-mercapto-2,3-dimethylbutanamide. Chiral GC of butanamide intermediate: 80.6% ee.

Aqueous concentrated HCl (30 mL) was warmed to 85° C. under an atmosphere of nitrogen. (S)-2-Mercapto-2,3-dimethylbutanamide was added as a solid and the mixture was stirred for 24 h. The solution was cooled to 23° C. and extracted using IPAC (3×20 mL). The combined organic phases were washed with brine, dried (Na$_2$SO$_4$) and concentrated under reduced pressure. Chromatographic purification (15 g silica gel, 10-40% EtOAc/Hexanes) of the residual material yielded 1.41 g (59%) of the title compound. $^1$H NMR (400 MHz, CDCl$_3$) δ 2.25 (septaplet, 1H, J=4 Hz), 2.22 (s, 1H), 1.43 (s, 3H), 1.09 (d, 3H, J=4 Hz), 0.98 (d, 3H, J=4 Hz); $^{13}$C NMR (100 MHz, CDCl$_3$) δ 181.5, 53.9, 36.4, 20.2, 18.2, 17.3; IR (neat): 2968, 2877, 1693, 1404, 1276, 1110, 925 cm$^{-1}$; Exact Mass (C$_6$H$_{12}$O$_2$S+Na): calculated=171.0450, measured=171.0449. [α]$_D$ at 23° C. and 26.0 g/L in CDCl$_3$=+3.18. MP=78-80° C.

Example 4

Preparation of 5S-2-(bicycle[2.2]heptan-2-ylamino)-5-isopropyl-5-methylthiazol-4(5H)-one (7)

(S)-2-Mercapto-2,3-dimethylbutanoic acid (1.5 g, 0.01 mol) was dissolved in toluene (15 mL) under an atmosphere of nitrogen. Activated 3A sieves (1.5 g) and MeSCN (1.1 mL, 0.015 mol) were added and the resultant mixture was warmed to 110° C. The mixture was stirred for 2 h and cooled to 23° C. The mixture was treated with saturated aqueous NaHCO$_3$ (20 mL), the phases were separated and the aqueous phase was extracted with EtOAc (3×15 mL). The combined organic phases were washed with brine, dried (Na$_2$SO$_4$) and concentrated under reduced pressure. Chromatographic purification (10 g silica gel, 20-30% EtOAc/Hexanes) of the residual material yielded (S)-5-isopropyl-5-methyl-2-(methylthio)thiazol-4(5H)-one. This material was dissolved in MeOH (15 mL) and (S)-exo-aminonorbornane (1.35 g, 0.015 mol, 99.3% ee) was added under an atmosphere of nitrogen. The solution was stirred for 4 h and concentrated. Chromatographic purification (10 g silica gel, 10-40% EtOAc/Hexanes) of the residual material yielded 1.73 g (64%) of the title compound. $^1$H NMR (400 MHz, CDCl$_3$, 90.15/9.85 mixture of diastereomers, signals for the major diastereomer) δ 3.33-3.40 (m, 1H), 2.36-2.45 (m, 2H), 2.21 (septaplet, 1H, J=8 Hz), 1.84-1.91 (m, 1H), 1.60-1.83 (m, 1H), 1.42-1.68 (m, 3H), 1.62 (s, 3H), 1.13-1.30 (m, 4H), 1.05 (d, 3H, J=8 Hz), 0.90 (d, 3H, J=8 Hz); $^{13}$C NMR (100 MHz, CDCl$_3$, 90.15/9.85 mixture of diastereomers, signals for the major diastereomer) δ 191.1, 180.9, 70.9, 59.5, 43.0, 38.5, 35.9, 35.7, 35.6, 28.2, 26.6, 25.6, 19.0, 18.4; IR (neat): 3168, 2959, 2869, 1696, 1585, 1440, 1327, 1256, 1090, 1017, 829 cm$^{-1}$; Exact Mass (C$_{14}$H$_{22}$N$_2$OS+H): calculated=267.1526, measured=267.1525. Chiral LC: 90.15/9.85 dr.

In another embodiment, synthesis of the target 5-substituted aminothiazolones is achieved via the asymmetric hydrocyanation of 3-methyl butane-2-one (1) to afford a cyanohydrin which is hydrolyzed to the corresponding acid (4), as shown in Scheme 2 below. Activation of the carboxylate group followed by reaction of the resultant acyl chloride with S-exo norbornylthiourea and intramolecular cyclization of the adduct under basic conditions afforded 5S-2-(bicycle [2.2.1]heptan-2-ylamino)-5-isopropyl-5-methylthiazol-4 (5H)-one as the product.

Scheme 2

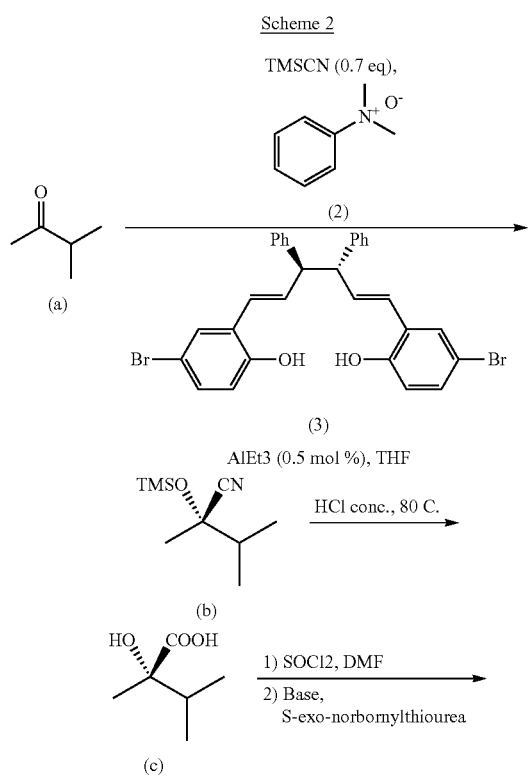

Example 5

Preparation of (S)-2,3-Dimethyl-2-(trimethylsilyloxy)butanenitrile (b)

TMSCN (28.8 g, 0.29 mol) and N,N-dimethylaniline oxide (0.2 g, 0.0015 mol) were dissolved in THF (75 mL) and the resultant solution was stirred for 1 h at 23° C. under an atmosphere of nitrogen. 3-Methylbutan-2-one (50.0 g, 0.58 mol) was added via syringe and the mixture was cooled to −30° C. 2-((E)-((1R,2R)-2-((E)-5-bromo-2-hydroxybenzylideneamino)-1,2-diphenylethylimino)methyl)-4-bromophenol (1.67 g, 0.0029 mol) and triethylaluminum (0.33 g, 0.0029 mol) were added and the reaction mixture was stirred for 24 h. The mixture was warmed to 23° C. and concentrated (30 mmHg). The residue was distilled under reduced pressure (30 mmHg, 80° C.) to yield 45.6 g (85%) of the title compound. $^1$H NMR (400 MHz, CDCl$_3$) δ 1.86 (septaplet, 1H, J=4 Hz), 1.53 (s, 3H), 1.04 (d, 3H, J=4 Hz), 1.02 (d, 3H, J=4 Hz), 0.25 (s, 9H); $^{13}$C NMR (100 MHz, CDCl$_3$) δ 121.5, 73.4, 39.1, 26.0, 17.1, 16.9, 1.15; IR (neat): 2969, 1375, 1254, 1160, 992, 841, 755 cm$^{-1}$; Exact Mass (C$_9$H$_{19}$NOSi+Na): calculated=208.1128, measured=208.1129. [α]$_D$ at 23° C. and 17.0 g/L in CDCl$_3$=−12.13. Chiral GC: 87.28% ee.

Example 6

Preparation of (S)-2-hydroxy-2,3-dimethylbutanoic acid (c)

Aqueous concentrated HCl (50 mL) was warmed to 85° C. under an atmosphere of nitrogen. (S)-2,3-Dimethyl-2-(trimethylsilyloxy)butanenitrile (5.0 g, 0.027 mol) was added and the mixture was stirred for 12 h. The solution was cooled to 23° C. and extracted using IPAC (3×50 mL). The combined organic phases were washed with brine, dried (Na$_2$SO$_4$) and concentrated under reduced pressure. Chromatographic purification (30 g silica gel, 10-50% EtOAc/Hexanes) of the residual material yielded 1.75 g (49%) of the title compound. $^1$H NMR (400 MHz, CDCl$_3$) δ 2.02 (septaplet, 1H, J=8 Hz), 1.44 (s, 3H), 1.00 (d, 3H, J=8 Hz), 0.93 (d, 3H, J=8 Hz); $^{13}$C NMR (100 MHz, CDCl$_3$) δ 182.1, 77.1, 35.5, 23.3, 17.2, 15.8; IR (neat): 3433, 2973, 2882, 1725, 1460, 1377, 1247, 1164, 1120, 1045, 948, 855, 737 cm$^{-1}$; Exact Mass (C$_6$H$_{12}$O$_3$+Na): calculated=155.0678, measured=155.0679. [α]$_D$ at 23° C. and 17.0 g/L in CDCl$_3$=+2.83. Chiral GC: 87.34% ee (measure using corresponding ethyl ester). MP=47-49° C. X-ray Crystal Structure Image of salt of (R)-2-hydroxy-2,3-dimethylbutanoic acid and R-α-methylbenzylamine is appended.

Example 7

Preparation of 5S-2-(bicycle[2.2.1]heptan-2-ylamino)-5-isopropyl-5-methylthiazol-4(5H)-one (d)

(S)-2-hydroxy-2,3-dimethylbutanoic acid (0.3 g, 0.0023 mol) was dissolved in DMF (1.5 mL) and 2-MeTHF (4.5 mL) under an atmosphere of nitrogen. POOMeCl$_2$ (0.34 g, 0.0023 mol) was added via syringe and the solution was stirred at 23° C. for 2.5 h. (S)-exo-Norbornylthiourea (0.27 g, 0.0016 mol, 99.2% ee) was added as a solid to the solution. iPr$_2$EtN (0.84 mL, 0.0046 mol) was immediately added dropwise via syringe and the resultant mixture was stirred for 12 h. The mixture was treated with saturated aqueous NaHCO$_3$ (10 mL), the phases were separated and the aqueous phase was extracted with EtOAc (3×15 mL). The combined organic phases were washed with brine, dried (Na$_2$SO$_4$) and concentrated under reduced pressure. Chromatographic purification (5 g silica gel, 10-30% EtOAc/Hexanes) of the residual material yielded 0.28 g (66%) of the title compound. $^1$H NMR (400 MHz, CDCl$_3$, 90.8/9.2 mixture of diastereomers, signals for the major diastereomer) δ 3.33-3.40 (m, 1H), 2.36-2.45 (m, 2H), 2.21 (septaplet, 1H, J=8 Hz), 1.84-1.91 (m, 1H), 1.60-1.83 (m, 1H), 1.42-1.68 (m, 3H), 1.62 (s, 3H), 1.13-1.30 (m, 4H), 1.05 (d, 3H, J=8 Hz), 0.90 (d, 3H, J=8 Hz); $^{13}$C NMR (100 MHz, CDCl$_3$, 90.8/9.2 mixture of diastereomers, signals for the major diastereomer) δ 191.1, 180.9, 70.9, 59.5, 43.0, 38.5, 35.9, 35.7, 35.6, 28.2, 26.6, 25.6, 19.0, 18.4; IR (neat): 3168, 2957, 1696, 1587, 1440, 1327, 1256, 1090, 1017, 834 cm$^{-1}$; Exact Mass (C$_{14}$H$_{22}$N$_2$OS+H): calculated=267.1526, measured=267.1525. Chiral LC: 90.8/9.2 dr.

We claim:

1. A process for the preparation of a compound of formula 4, or a tautomer, stereoisomer or pharmaceutically acceptable salt thereof:

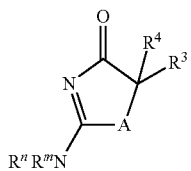

comprising reacting a compound of formula 5:

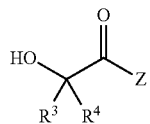

with a compound of formula 6

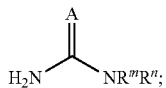

wherein
- A is S;
- Z is selected from the group consisting of a halogen, $OR^6$ and $SR^6$;
- $R^3$ and $R^4$ are each independently selected from the group consisting of hydrogen, $(C_1-C_8)$alkyl, $(C_2-C_8)$alkenyl, $(C_2-C_8)$alkynyl, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$aminoalkyl, $(C_3-C_8)$haloalkyl, $(C_3-C_8)$heteroalkyl, $(C_3-C_8)$ heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, and aryl$(C_1-C_6)$alkyl; wherein $R^3$ and $R^4$ are not simultaneously hydrogen;
- $R^5$ is selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl;
- $R^6$ is selected from the group consisting of hydrogen, $(C_1-C_8)$alkyl, pentafluorophenyl, nitrophenyl, di-nitrophenyl, $CF_3$phenyl, p-toluenesulfonyl, and methanesulfonyl;
- $R'''$ is selected from the group consisting of hydrogen, $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl; and
- $R''$ is selected from the group consisting of $(C_1-C_8)$alkyl, $(C_2-C_8)$alkenyl, $(C_2-C_8)$alkynyl, $(C_1-C_4)$alkoxy, $(C_1-C_4)$alkoxy$(C_1-C_4)$alkyl, $(C_1-C_8)$fluoroalkyl, $(C_1-C_8)$hydroxyalkyl, $(C_3-C_8)$cycloalkyl, $(C_4-C_8)$bicycloalkyl, $(C_3-C_8)$heterocycloalkyl, heteroaryl, aryl, $(C_3-C_8)$cycloalkyl$(C_1-C_6)$alkyl, $(C_3-C_8)$heterocycloalkyl$(C_1-C_6)$alkyl, heteroaryl$(C_1-C_6)$alkyl and aryl$(C_1-C_6)$alkyl.

2. The process of claim 1, wherein $R^3$ and $R^4$ are independently selected from $(C_1-C_8)$alkyl.

3. The process of claim 1, wherein $R'''$ is H.

4. The process of claim 1, wherein the compound of formula 5 is (S)-2-hydroxy-2,3-dimethyl butanoic acid, and the compound of formula 6 is (S)-exo-Norbornylthiourea.

5. The process of claim 1, wherein the compound of formula 4 is

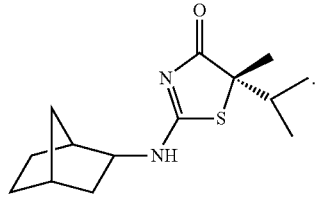 [SMILES: CC(C)[C@]1(C)SC(NC2CC3CCC2C3)=NC1=O]

* * * * *